United States Patent [19]

Matthews

[11] Patent Number: 5,741,212

[45] Date of Patent: Apr. 21, 1998

[54] BLEMISH ASSESSOR

[76] Inventor: Michael Weston Bertie Matthews, 37 Manor Road., Dorchester, Dorset, DT1 2AY, United Kingdom

[21] Appl. No.: 700,517

[22] PCT Filed: Mar. 3, 1995

[86] PCT No.: PCT/GB95/00466

§ 371 Date: Aug. 21, 1996

§ 102(e) Date: Aug. 21, 1996

[87] PCT Pub. No.: WO95/23553

PCT Pub. Date: Sep. 8, 1995

[30] Foreign Application Priority Data

Mar. 4, 1994 [GB] United Kingdom ............... 9404235

[51] Int. Cl.$^6$ ........................................... A61B 5/107
[52] U.S. Cl. ........................................... 600/300; 33/512
[58] Field of Search ........................... 128/630, 897, 128/898, 774; 602/42; 33/511, 512, 562, 565, 15 D

[56] References Cited

U.S. PATENT DOCUMENTS

| | | | |
|---|---|---|---|
| 4,090,501 | 5/1978 | Chaitin | 128/2 H |
| 4,131,998 | 1/1979 | Spears | 128/774 |
| 4,279,259 | 7/1981 | Lee | 128/774 |
| 4,389,782 | 6/1983 | Webster | 33/512 |
| 4,483,075 | 11/1984 | Kundin | 33/512 |
| 5,000,172 | 3/1991 | Ward | 602/57 |
| 5,265,605 | 11/1993 | Afflerbach | 128/630 |

FOREIGN PATENT DOCUMENTS 9214402  9/1992  WIPO.

*Primary Examiner*—Jennifer Bahr
*Assistant Examiner*—David M. Ruddy
*Attorney, Agent, or Firm*—Edwin D. Schindler

[57] ABSTRACT

A device for use in assessing various characteristics of a skin blemish, which includes at least two blemish assessment discs mounted for relative movement, with each assessment disc carrying a scale of blemish criteria so that the skin blemish may be positioned adjacent the scales of each assessment disc and matched with the relevant portions thereof.

24 Claims, 3 Drawing Sheets

5,741,212

BLEMISH ASSESSOR

This invention relates to a blemish assessor, for example a device for use in assessing changing conditions in skin blemishes, particularly but not exclusively of pigmented spots or moles.

It is important in the assessment and/or treatment of skin blemishes such as those commonly known as moles to detect changes in those abnormalities at an early stage. Such changes often give an early suspicion of possible malignancy.

It is difficult to assess such changes as eg increase in size, shape, colour or thickness by memory and a person may either wishfully see no change in condition or, alternatively generate unwarranted alarm by imagining changes that are not in fact occurring.

Prior proposals in this field include: GB-A-2,159,943, U.S. Pat No. 4,422,759, GB-A-2. 164,447 and U.S. Pat. No. 4,905,702.

There is described in WO-A-92/14402 a device for assessing a skin blemish comprising a multi-functional tool having a colour scale along one edge and a size scale along its opposite edge, together with a distance scale for recording the distance of a blemish from a fixed reference point.

None of the above prior proposals discloses a convenient means for identifying a skin blemish and conveniently assessing it in relation to two or more of its characteristics substantially simultaneously.

It is an object of this invention to provide means for enabling any such changes to be readily and accurately assessed and for assisting in recording such changes, and/or to provide improvements generally in relation to the above or related requirements.

In accordance with the invention there is provided a device for the assessment of skin blemishes, as defined in the accompanying claims.

In accordance with the invention there is provided a device for enabling measurements to be made in respect of various characteristics of a skin blemish as claimed in the accompanying claims.

In an embodiment a device for the assessment of skin blemishes comprises at least two blemish assessment elements. Each assessment element comprises a graded or graduated scale or sequence of blemish criteria. The assessment elements are mounted for movement relative to each other and alongside each other, whereby a skin blemish may be positioned adjacent both scales or sequences and matched with the relevant portion of the scale or sequence of blemish criteria on each scale simultaneously. In this way, a systematic approach to assessment of blemish criteria is provided which avoids the uncertainties of comparison with criteria by memory and the uncertainty arising from carrying out assessments at time-spaced intervals.

In the embodiment, the assessment elements are of circular form and mounted for rotation relative to each other, with the scales or sequences of blemish criteria extending in circular or arcuate form likewise. In this way, a device of compact and convenient form is provided.

Also in the embodiment, the assessment elements are adapted to enable a blemish to be visually assessed while positioned below the device by having the assessment elements formed with apertures and/or comprising at least portions of a transparent material. Accordingly, this enables a blemish to be positioned adjacent both scales of the device conveniently and effectively for visual assessment purposes.

Also in the embodiment, the scales or sequences of blemish criteria comprise size criteria and colour criteria and degree of acuteness criteria. The latter includes such criteria as itching, inflammation, bleeding, crusting, irregular outline, and colour variation.

For the assessment of size, the embodiment provides a sequence of defined closed shapes, such as circles, of graded sizes. This represents a convenient and effective mode of size-assessment.

For assessment of depth criteria, the device comprises depth-matching portions, for example of tapering or differing depth, on one of the assessment elements, which portions carry depth data and can be matched with the depth of the blemish in question.

According to another aspect of the invention there is provided a device for assessment of skin blemishes comprising first and second moveable assessment elements. The first assessment element, for example in the form of a base plate, comprises a plurality of apertures of differing sizes to enable a skin blemish to be identified and/or size-assessed. A second assessment element comprises assessment means for another characteristic of a skin blemish, for example colour. The assessment elements may be provided with means for assessing other characteristics, including thickness of the blemish, its area, and otherwise. The relevant part or parts of the second assessment element are moveable relative to the first assessment element to enable assessment by the second element to be performed alongside the blemish after it has been identified by location of one of said apertures of said first assessment element over the blemish.

The first assessment element, for example in the form of a base plate, may be circular and the second assessment may be mounted for rotation over the base plate member, the second assessment element being provided with, for example, a plurality of segments or sectors coloured in different shades, or graded in colour or intensity, and adapted to be used to compare with and record the colour of the skin blemishes.

Further segments or sectors on the second element may be provided and marked to remind the user or observer of various other characteristics which should be assessed in sequence.

The base member may be provided with further means for-use in measuring the thickness of the skin blemish.

The assessment device may be provided with means for visual magnification of the skin blemish, for example in the form of a magnifying lens mounted on the device at a location spaced above the blemish itself, when the device is in use.

Embodiments of the invention will now be described by way of example with reference to the accompanying drawings in which.

Figure 1:
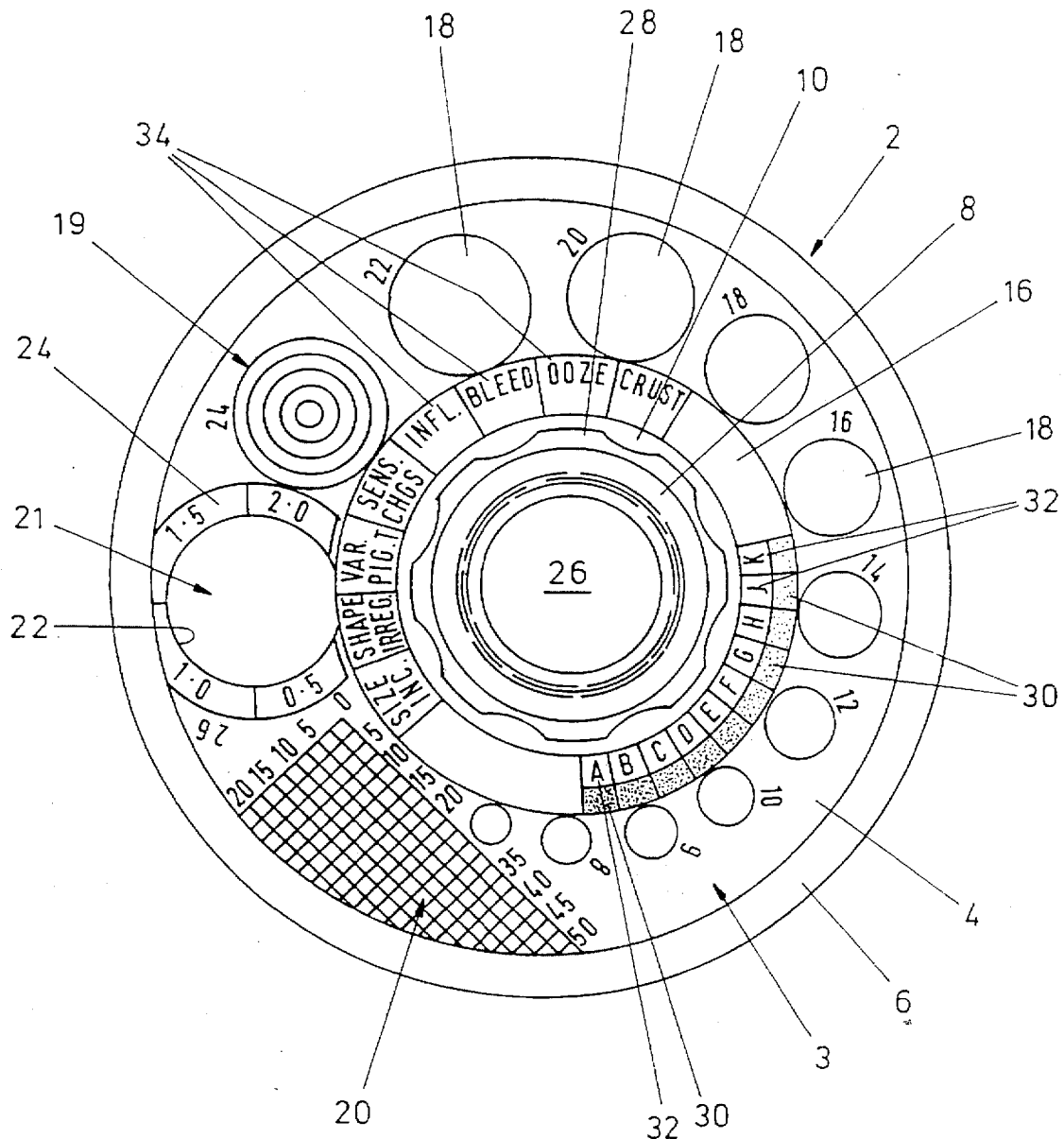
FIG. 1 is a plan view of an assessor according to the invention.

As seen in the drawings a skin blemish assessing instrument 2 comprises a first assessment element 3 comprising a circular disc-like base 4 having a rim 6 and an upstanding central boss 8.

Mounted for rotation around the boss 8 is a second assessment element 10 having an annular tongue 12 which depends downwardly into a mating annular groove 14 formed in the base 4.

A flange 16 extends from the base of the second assessment element 10.

The disc-like base 4 is formed with a series of holes each of a different diameter and the size in millimeters of each hole is marked eg by embossment alongside the hole. A plurality of concentric circles indicated at 19 is embossed on the upper surface of the base 4 and a grid 20 is also embossed as shown.

Blemish thickness assessment means 21 comprises an opening or hole 22 which is larger in diameter than any of the holes 18 is formed also in the base 4 and an annulus 24 is formed upstanding around the hole 22. This annulus is formed in segments 24 each having a different height from the underside of the base 4 and each segment is marked with that dimension.

The boss 8 has an upper surface 26 moulded in shape to provide a magnifying glass.

Figure 3:
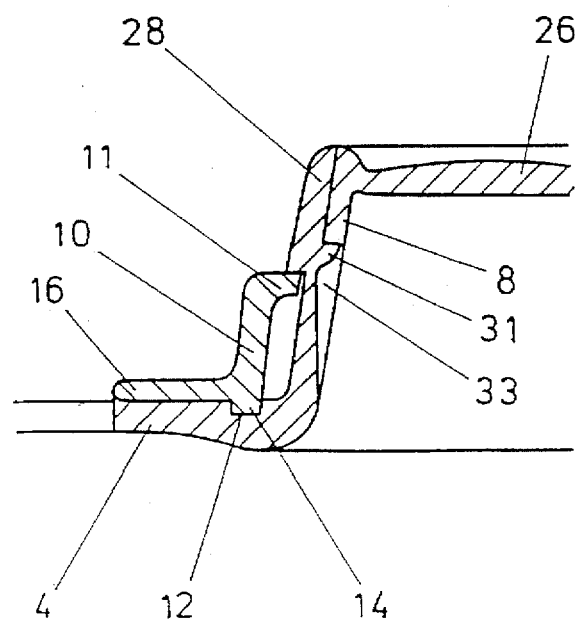
FIG. 3 is an enlarged section view of parts seen in FIG. 2.

The second assessment element 10 has an in-turned flange which fits around the boss 8 of the base member 4 and is retained thereon by a capping piece 28. As seen in FIG. 3 a tooth 31 is snapped into one of the a number of recesses 33 formed in the boss 8 and while retaining the element 10 allows it to rotate about the vertical axis of the boss with the annular tongue 12 being guided in the groove 14.

The circumferential periphery of the flange 16 is arranged to align with the peripheries of the holes 18.

The flange 16 of the second assessment element 10 is provided with certain areas of information which is to be checked and recorded during examination of the skin blemish being assessed. For example, as seen in FIG. 1 some segments 30 of the flange are coloured in shades varying from black through different shades of brown and including shades of red and purple.

Further segments 34 of the flange are marked with other information to be checked and recorded, eg increase in size, irregular shape, pigment shade or shades, inflammation, oozing, bleeding, crusting, increase or decrease in height, increase in area.

In use the assessing instrument 2 is placed on the skin of the user and moved until a hole 18 on first assessment element 3 overlies a skin blemish eg a mole, of the same diameter and that diameter is recorded on a chart (not shown). It may be that the blemish is not truly circular in which case more than one hole 18 is used to provide measurements of the major and minor axes which will then be recorded.

The second assessment element 10 is then rotated step-by-step until the appropriate coloured segment 30 on the flange 16 is located alongside and matches the pigmentation of the mole as seen through the relevant one of the holes 18. This is then also recorded by means of code letters 32 associated with the coloured pigments.

The further segments 34 on second assessment 10 are then aligned, in turn, with the appropriate hole above the mole and a check is made on each of the conditions enumerated in the segment, ie has the blemish increased in size since the last previous examination, has it changed shape, is it inflamed, bleeding, etc?

The area of the blemish may be measured with a fair amount of accuracy by placing the grid 20 of element 3 over the blemish and counting the number of squares which overlie the blemish, counting in the accepted method of approximation, each square which is complete or more than one half complete as 1, and each square which is less than one half complete as 0. Such area is also recorded and checked against the area measurement taken at the last previous assessment to assess any change in area. The areas of different pigmentation on a mole may also be readily assessed by utilising this grid.

The hole 22 of thickness assessor 21 is then placed over the mole and the heights of the segments 24 are compared with the height above the skin of the mole. Such a measurement is recorded and compared with the record of the last previous height measurement to assess any change in that regard.

The components of the instrument are preferably made of a clear optical grade polycarbonate or similar material and formed by an injection moulding process.

It is intended that the instrument may be used by a patient as well as by a general practitioner. When the patient recognises significant changes in appearance of a mole by using the instrument he should of course then consult his general practitioner giving details of the changes noted. This will assist the general practitioner in his diagnosis.

For professional use, ie by a general practitioner, certain numerical "scores" may be given for certain features and may be shown on the device. For example, features present such as increase in size, irregular shape and several shades of pigment would score 2 whilst minor features present such as sensory change, inflammation, bleeding, would score 1. The higher the accumulated score, the greater is the index of suspicion of malignancy.

Figure 4:
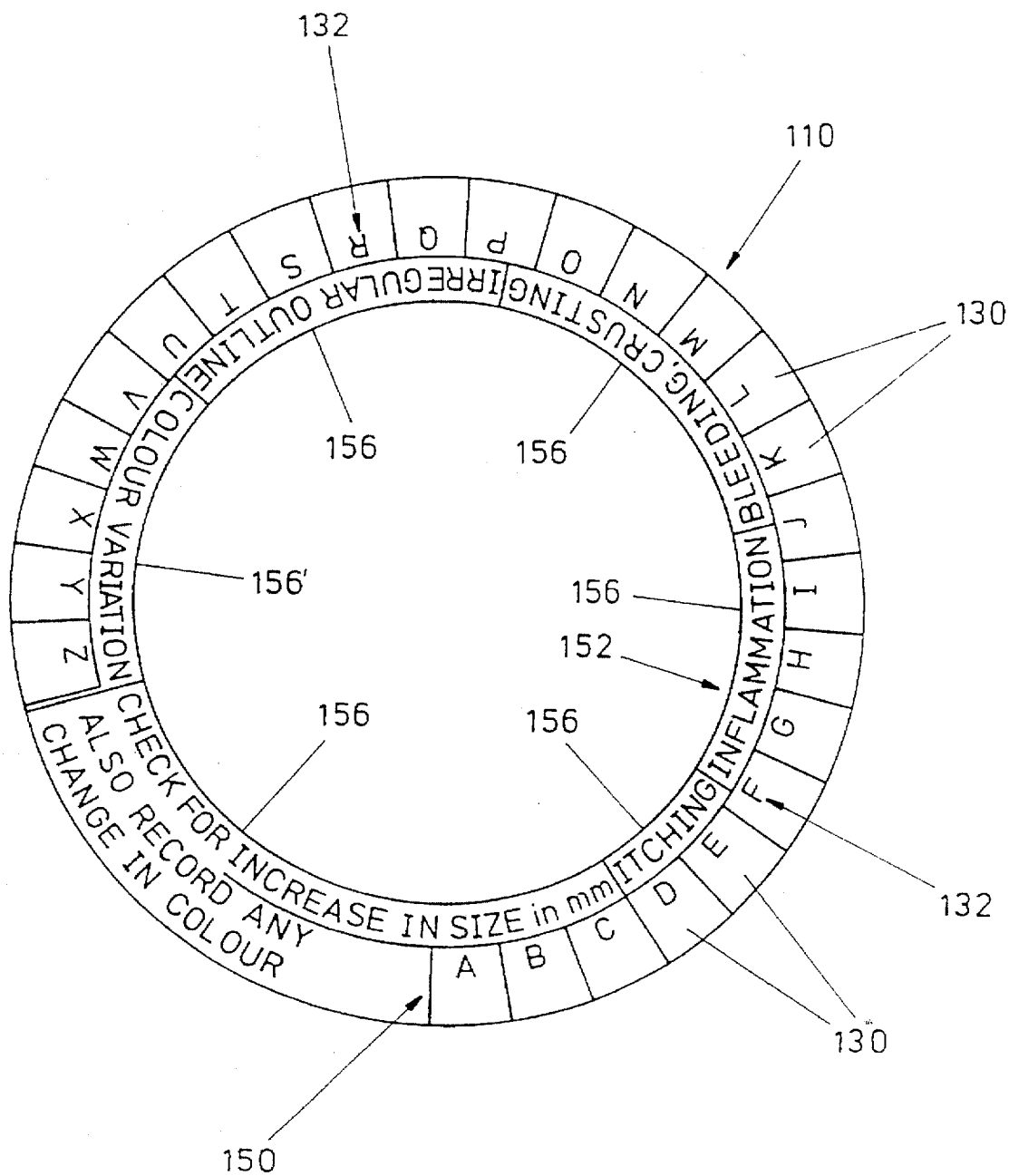
FIG. 4 is a plan view of an alternative second assessment element having modified scales or sequences of blemish criteria.

In the embodiment of FIG. 4, the second assessment element 10 is replaced by an alternative second assessment element 110 in which parts corresponding to those of the assessment element 10 are allocated the same reference numerals increased by 100. Thus, assessment element 110 comprises segments 130 of the flange which are coloured in varying shades from black through brown to red and purple. Each segment 130 is provided with an identifying letter 132 from A to Z, and thus in this embodiment, a significantly greater number of different shades are provided whereby matching with a given blemish is facilitated.

Thus, segments 130 and their identifiers 132 constitute one graded or graduated scale or sequence 150 of blemish criteria. There is provided, in addition, a second scale or sequence of blemish criteria 152 positioned radially inwardly of scale 150 at the inner periphery of second blemish assessment element 110. Scale 152 comprises segments 156, each with its associated text, identifying further blemish assessment criteria for consideration by the practitioner, in sequence. Thus, segments 156 correspond to the further segments 34 of the preceding embodiment.

Figure 2:
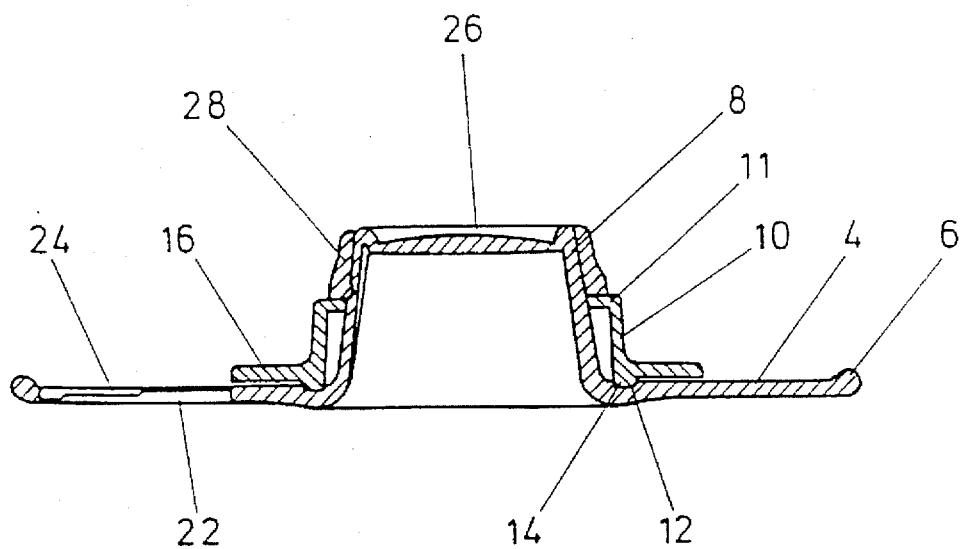
FIG. 2 is a section view on the line II—II of FIG. 1.

In this embodiment, the assessment element 110 is mounted in association with the first assessment element 3, generally in the manner illustrated in FIGS. 1 to 3, and is used in association with that assessment element, as described above.

In this embodiment, assessment element 110 is generally in the form of a flat disc and thus details of its mounting in relation to the first assessment element differ somewhat from those shown in FIGS. 1 to 3, but these are merely simply mechanical mounting details which are well within the competence of the man skilled in the art, without further description here.

Amongst other modifications which could be made in the above embodiments while remaining within the scope of the invention are the following. Firstly, changes in the positions and relative dispositions of the blemish assessment devices on the first and second assessment elements may be made to suit particular needs. The rotatable second assessment element may be constructed to enable assessment of other blemish criteria. Its main function is to enable such assessment of other criteria to be performed in relation to an identified blemish which is in an assessment relation with the first assessment element. The form of the overall device is susceptible to change, and indeed other materials may be employed. So far as the provision of magnification means is concerned, it may be convenient to provide, as an alternative or an addition to the central magnification lens, such a lens which could be positioned directly over a blemish which is being assessed by the first and second assessment elements.

I claim:

1. A device for the assessment of skin blemishes, comprising:

at least two blemish assessment elements, each of said blemish assessment elements being circular and having a circular or arcuate-form graduated scale, or sequence, of blemish criteria, said blemish assessment elements mounted for rotational movement relative to each other and alongside each other, so that a skin blemish is able to be positioned adjacent the graduated scale, or the sequence, of blemish criteria of each said blemish assessment element and thereby matched with a relevant portion of the graduated scale, or the sequence, of blemish criteria on each blemish assessment element simultaneously; and, a lens mounted centrally of said blemish assessment elements for optically inspecting a blemish.

2. The device for the assessment of skin blemishes according to claim 1, wherein the graduated scale, or the sequence, of blemish criteria of each said blemish assessment element include at least one of size criteria or color criteria or degree of acuteness criteria.

3. The device for the assessment of skin blemishes according to claim 2, wherein the size criteria of the graduated scale, or the sequence, of blemish criteria of each said blemish assessment element includes a transparent grid pattern zone adapted for assisting assessment of a blemish area by permitting a counting of grid zones.

4. The device for the assessment of skin blemishes according to claim 2, wherein the size criteria of the graduated scale, or the sequence, of blemish criteria of each said blemish assessment element include depth criteria defined by at least one depth-matching portion.

5. The device for the assessment of skin blemishes according to claim 1, wherein the graduated scale, or the sequence, of blemish criteria of each said blemish assessment element include a sequence of defined closed shapes or graded sizes.

6. The device for the assessment of skin blemishes according to claim 1, wherein one of said blemish assessment elements includes a plurality of apertures of differing size for enabling a skin blemish to be identified and size-assessed.

7. A device for the assessment of skin blemishes, comprising:

at least two blemish assessment elements, each of said blemish assessment elements having a graduated scale, or sequence, of blemish criteria, said blemish assessment elements mounted for movement relative to each other and alongside each other, so that a skin blemish is able to be positioned adjacent the graduated scale, or the sequence, of blemish criteria of each said blemish assessment element and thereby matched with a relevant portion of the graduated scale, or the sequence, of blemish criteria on each blemish assessment element simultaneously, one of said blemish assessment elements further including a plurality of apertures of differing size for enabling a skin blemish to be identified and size-assessed.

8. The device for the assessment of skin blemishes according to claim 7, wherein said blemish assessment elements are circular in shape and mounted for rotational movement relative to each other with the graduated scale, or the sequence, of blemish criteria extending in a circular, or arcuate, form.

9. The device for the assessment of skin blemishes according to claim 7, wherein the graduated scale, or the sequence, of blemish criteria of each said blemish assessment element include at least one of size criteria or color criteria or degree of acuteness criteria.

10. The device for the assessment of skin blemishes according to claim 9, wherein the size criteria of the graduated scale, or the sequence, of blemish criteria of each said blemish assessment element includes a transparent grid pattern zone adapted for assisting assessment of a blemish area by permitting a counting of grid zones.

11. The device for the assessment of skin blemishes according to claim 9, wherein the size criteria of the graduated scale, or the sequence, of blemish criteria of each said blemish assessment element include depth criteria defined by at least one depth-matching portion.

12. The device for the assessment of skin blemishes according to claim 7, wherein the graduated scale, or the sequence, of blemish criteria of each said blemish assessment element include a sequence of defined closed shapes or graded sizes.

13. The device for the assessment of skin blemishes according to claim 7, further comprising a lens mounted centrally of said blemish assessment elements for optically inspecting a blemish.

14. A device for the assessment of skin blemishes, comprising:

at least two blemish assessment elements, each of said blemish assessment elements having a graduated scale, or sequence, of blemish criteria, said blemish criteria including a size criteria having a transparent grid pattern zone adapted for assisting assessment of a blemish area by permitting a counting of grid zones, said blemish assessment elements mounted for movement relative to each other and alongside each other, so that a skin blemish is able to be positioned adjacent the graduated scale, or the sequence, of blemish criteria of each said blemish assessment element and thereby matched with a relevant portion of the graduated scale, or the sequence, of blemish criteria on each blemish assessment element simultaneously; and, a lens mounted centrally of said blemish assessment elements for optically inspecting a blemish.

15. The device for the assessment of skin blemishes according to claim 14, wherein said blemish assessment elements are circular in shape and mounted for rotational movement relative to each other with the graduated scale, or the sequence, of blemish criteria extending in a circular, or arcuate, form.

16. The device for the assessment of skin blemishes according to claim 14, wherein the graduated scale, or the sequence, of blemish criteria of each said blemish assessment element further includes at least one of color criteria or degree of acuteness criteria.

17. The device for the assessment of skin blemishes according to claim 14, wherein the size criteria of the graduated scale, or the sequence, of blemish criteria of each said blemish assessment element include depth criteria defined by at least one depth-matching portion.

18. The device for the assessment of skin blemishes according to claim 14, wherein the graduated scale, or the sequence, of blemish criteria of each said blemish assessment element include a sequence of defined closed shapes or graded sizes.

19. The device for the assessment of skin blemishes according to claim 14, wherein one of said blemish assessment elements includes a plurality of apertures of differing size for enabling a skin blemish to be identified and size-assessed.

20. A device for the assessment of skin blemishes, comprising:

at least two blemish assessment elements, each of said blemish assessment elements having a graduated scale, or sequence, of blemish criteria, said blemish criteria including a size criteria having a transparent grid pattern zone adapted for assisting assessment of a blemish area by permitting a counting of grid zones, said blemish assessment elements mounted for movement relative to each other and alongside each other, so that a skin blemish is able to be positioned adjacent the graduated scale, or the sequence, of blemish criteria of each said blemish assessment element and thereby matched with a relevant portion of the graduated scale, or the sequence, of blemish criteria on each blemish assessment element simultaneously, wherein one of said blemish assessment elements includes a plurality of apertures of differing size for enabling a skin blemish to be identified and size-assessed.

21. The device for the assessment of skin blemishes according to claim 20, wherein said blemish assessment elements are circular in shape and mounted for rotational movement relative to each other with the graduated scale, or the sequence, of blemish criteria extending in a circular, or arcuate, form.

22. The device for the assessment of skin blemishes according to claim 20, wherein the graduated scale, or the sequence, of blemish criteria of each said blemish assessment element further includes at least one of color criteria or degree of acuteness criteria.

23. The device for the assessment of skin blemishes according to claim 20, wherein the size criteria of the graduated scale, or the sequence, of blemish criteria of each said blemish assessment element include depth criteria defined by at least one depth-matching portion.

24. The device for the assessment of skin blemishes according to claim 20, wherein the graduated scale, or the sequence, of blemish criteria of each said blemish assessment element include a sequence of defined closed shapes or graded sizes.

* * * * *